United States Patent [19]
Kurz et al.

[11] Patent Number: 5,656,262
[45] Date of Patent: Aug. 12, 1997

[54] SKIN-COLORING POWDER MIXTURE

[75] Inventors: Thekla Kurz, Grosse-Zimmern; Sabine Hitzel, Messel; Roland Martin, Weinheim; Ralf Emmert, Dieburg, all of Germany

[73] Assignee: Merck Patent Gesellschaft mit beschrankter Haftung, Darmstadt, Germany

[21] Appl. No.: 234,795

[22] Filed: Apr. 28, 1994

[30]     Foreign Application Priority Data

Apr. 29, 1993 [DE]  Germany ................... 43 14 083.1

[51] Int. Cl.$^6$ ........................................... A61K 7/42
[52] U.S. Cl. ..................... 424/59; 424/45; 424/401
[58] Field of Search ....................... 424/401, 59, 45

[56]                 References Cited

U.S. PATENT DOCUMENTS

| | | | |
|---|---|---|---|
| 2,949,403 | 8/1960 | Andreadis et al. | 167/90 |
| 3,506,758 | 4/1970 | Epstein et al. | 424/60 |
| 5,049,381 | 9/1991 | Schultz et al. | 424/401 |
| 5,232,688 | 8/1993 | Ziegler et al. | 424/59 |

FOREIGN PATENT DOCUMENTS

| | | |
|---|---|---|
| 77959 | 5/1983 | European Pat. Off. . |
| 456545 | 11/1991 | European Pat. Off. . |
| 500446 | 8/1992 | European Pat. Off. . |
| 2085208 | 12/1971 | France . |
| 54-132243 | 10/1979 | Japan . |

OTHER PUBLICATIONS

Abstract of JP 54–132243. (Oct. 15, 1979).
Abstract of EP 77,959. (May 4, 1983).
Abstract of FR 2,085,208. (Dec. 24, 1971).
Abstract of EP 500,446. (Aug. 26, 1992).
Abstract of EP 456,545. Nov. 13, 1991.

*Primary Examiner*—Jyothsna Venkat
*Attorney, Agent, or Firm*—Millen, White, Zelano, & Branigan, P.C.

[57]                 ABSTRACT

The invention relates to powder mixtures containing formaldehyde- and/or formic acid-releasing compounds which have skin-tanning properties, which powder mixtures contain an agent which forms sulphite ions and, if appropriate, a stabilizer, and to the preparation and use of these powder mixtures for manufacturing cosmetic or pharmaceutical preparations.

10 Claims, No Drawings

SKIN-COLORING POWDER MIXTURE

BACKGROUND OF THE INVENTION

The invention relates to a powder mixture, containing formaldehyde- and/or formic acid-releasing compounds which have skin-tanning properties, which powder mixture contains an agent which forms sulphite ions.

It has been known for some time that compounds which have a ketol group

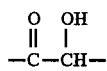

preferably hydroxymethyl ketones, in particular dihydroxyacetone, have a self-tanning effect on human skin. This self-tanning effect is essentially based on a Maillard reaction between the ketol group of these compounds and the amino acids of the skin.

The hue obtained in this reaction can be further enhanced by adding certain adjuvants (for example EP 0 425 324).

Moreover, WO 91/12222 proposes to stabilize dihydroxyacetone (DHA) by coating at least part of it, in its dimeric form, with a water-impermeable composition. This publication furthermore proposes to employ formal-dehyde-releasing compounds to prevent the bacterial degradation of DHA.

SUMMARY OF THE INVENTION

It has now been found that compounds, such as, for example, DHA, which have a ketol group, slowly release formaldehyde and/or formic acid in the cosmetic preparations. These are, in general, traces of formaldehyde or formic acid,. i.e. formaldehyde contents of a few ppm, as a rule, 20–100 ppm.

It was therefore an object of the present invention to find pulverulent components which can be processed to give stable mixtures, in which the formation of formaldehyde and formic acid is completely suppressed.

Surprisingly, it has been found that, using agents which form sulphite ions, e.g., a source of sulfite ions, the formation of formaldehyde and formic acid can be completely suppressed in such pulverulent components and in formulations made with them.

The invention therefore relates to a powder mixture containing formaldehyde- and/or formic acid-releasing compounds which have skin-tamping properties, which powder mixture contains an agent which forms sulphite ions and, if appropriate, stabilizer.

The invention furthermore relates to the use of such a mixture in the manufacture of cosmetic or pharmaceutical preparations.

The invention furthermore also relates to the preparation of these mixtures, where at least one of the components, in particular the agent forming sulphite ions, is triturated or coated with the stabilizer.

The following are preferred embodiments:
a) mixtures in which the compound which has skin-tanning properties is dihydroxyacetone;
b) mixtures in which the agent which forms sulphite ions is a hydrogen sulphite, disulphite or dithionite, preferably an alkali metal hydrogen sulphite, alkaline earth metal hydrogen sulphite, alkali metal disulphite or alkali metal dithionite, in particular sodium hydrogen sulphite, sodium bisulfite or sodium dithionite;
c) mixtures which contain 45 to 99, preferably 80 to 90, % by weight of a formaldehyde- and/or formic acid-releasing compound (i.e., a compound with self-tanning properties), 0.1 to 50, preferably 1 to 20, % by weight of an agent which forms sulphite ions, and 0.1 to 5% by weight of a stabilizer, e.g., one which prevents the decomposition of the self-tanning compound, as described in WO 91/12222, in each case based on the total mixture;
d) mixtures in which the ratio by weight between the agent which forms sulphite ions and the formaldehyde- and/or formic acid-releasing compound is greater than 0.01;
e) mixtures which contain, as stabilizer, a stearate, in particular magnesium stearate;
f) mixtures which contain, as stabilizer, a film-forming agent;
g) mixtures which contain, as stabilizer, a cellulose derivative, in particular ethylcellulose or nitrocellulose;
h) mixtures which contain, as stabilizer, a higher alcohol, such as, for example, cetyl alcohol, a paraffin or another, conventional polymeric coating material.

Preferred compounds which have skin-tanning properties are those having a ketol group

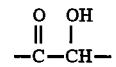

in particular dihydroxyacetone.

Preferred agents which form sulphite ions are metal sulphites, metal disulphites or metal hydrogen sulphites and metal dithionites, such as, for example, sodium hydrogen sulphite, calcium hydrogen sulphite, sodium sulphite, potassium sulphite, sodium dithionite, zinc dithionite and sodium disulphite.

The mixture according to the invention is preferably employed in the manufacture of cosmetic preparations as a composition for taming the human epidermis. Such a composition is in various forms which are conventionally used for this type. For example, it can be, in particular, in the form of oily or oily/alcoholic lotions, emulsions, such as a cream or a milk, in the form of oily/alcoholic, oily/aqueous or aqueous/alcoholic gels or in the form of solid sticks or else formulated as an aerosol.

It may contain cosmetic adjuvants which are conventionally used in this type of composition, such as, for example, thickeners, plasticizers, humectants, surfactants, fungicides, bactericides, preservatives, in particular alkyl 4-hydroxybenzoates, antifoams, perfumes, waxes, lanolin, propellants, colorants and/or pigments which impart color to the composition itself, UV filters for the protection against UV-A and/or UV-B rays and other ingredients customarily used in cosmetology.

It is highly preferred that the preparations according to the invention do not contain formaldehyde or formaldehyde-releasing compounds as bactericides.

An oil, wax or other fatty substance, a lower monoalcohol or a lower polyol or mixtures of these may be used as solubilizers. The particularly preferred monoalcohols or polyols include ethanol, i-propanol, propylene glycol, glycerol and sorbitol.

A preferred embodiment is an emulsion in the form of a cream or milk and includes, in addition to the skin-tanning compound, fatty alcohols, fatty acid esters, in particular fatty acid triglycerides, fatty acids, lanolin, natural or synthetic oils or waxes and emulsifiers in the presence of water.

Other preferred embodiments are oily lotions based on natural or synthetic oils and waxes, lanolin; fatty acid esters, in particular fatty acid triglycerides, or oily/alcoholic lotions based on a lower alcohol, such as ethanol, or a glycol, such as propylene glycol and/or a polyol, such as glycerol, and oils, waxes and fatty acid esters, such as fatty acid triglycerides.

The cosmetic composition can also be in the form of an alcoholic or aqueous gel which includes one or more lower alcohols or lower polyols, such as ethanol, propylene glycol or glycerol, and a thickener, such as silica.

The oily/alcoholic gels additionally contain a natural or synthetic oil or wax.

The solid sticks are composed of natural or synthetic waxes and oils, fatty alcohols, fatty acid esters, lanolin and other fatty substances.

Other suitable compositions are cosmetic sunscreen products which include at least one UV-B and/or UV-A filter.

Examples of suitable UV filters are cinnamic acid derivatives, benzylidenecamphor and its derivatives, p-aminobenzoic acid and its derivatives, salicylic acid derivatives, benzophenone derivatives and dibenzoylmethane derivatives. As a rule, the preparations contain 0.2 to 10% by weight of these UV filters.

If a preparation is formulated as an aerosol, the conventional propellants, such as alkanes, fluoroalkanes chlorofluoroalkanes are generally used.

If appropriate, the preparation may contain thickeners:

The thickeners or gelling agents known to the person skilled in the art can be used for thickening, examples being guar gum, heterobiopolysaccharides, xanthan gum, scleroglucans, cellulose derivatives, such as, for example, methylcellulose, hydroxyethylcellulose, hydroxymethylpropylcellulose, alkali metal salts of carboxymethylcellulose, and polyacrylic acids.

The mixtures according to the invention can be prepared by a range of processes known per se to the expert. This is because it has emerged, surprisingly, that all that is necessary for achieving a stabilizing effect is that contact between the individual components of the powder, i.e., the compound with self-tanning properties and/or the source of sulfite ions, is not too intimate.

Suitable stabilizers are therefore, for example, conventional lubricants, such as, for example, stearates, with which at least one of the powder components is triturated or ground. The at least partial coverage of the surface of the powder component, the self-tanning compound or the sulfite ion source, with the stabilizer achieved in this process suffices for the stabilization required. This trituration of the powder component with a lubricant can be carried out in conventional devices and mixers which are known to a person skilled in the art.

However, other agents which can be used for the stabilization are all conventional film-forming agents, such as, for example, cellulose derivatives, higher alcohols, paraffins and polymers. These agents are conventionally dissolved in a suitable solvent. Granules which can then be mixed with the second component are obtained by making the powder component into a paste together with the solution and subsequently drying and screening the product. However, it is also possible to spray, in a mixer, the powder component with the solution of the film-forming agent and drying the product, or other processes known to a person skilled in the art can be used.

It is preferred that at least one of the powder components is treated with the stabilizer. The question of which of the two components is to be treated can be decided by a person skilled in the art from a practical point of view, for example according to which component can be treated more easily in conventional mixers or granulating devices. Of course, it is also possible to treat both powder components.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. P 43 14 083.1, filed Apr. 29, 1993 is hereby incorporated by reference.

EXAMPLES

Example 1

In a mixer, 10 g of sodium sulphite are triturated vigorously with 0.5 g of magnesium stearate, and subsequently mixed with 89.5 g of dihydroxyacetone. This gives a storage-stable powder mixture which can be employed immediately for the manufacture of cosmetic preparations.

Example 2

The procedure is analogous to Example 1, but sodium disulphite is used in place of sodium sulphite.

Examples 3 and 4

The procedure is analogous to Examples 1 and 2, but calcium stearate is used in place of magnesium stearate.

Example 5

98 g of dihydroxyacetone and a solution of 2 g of ethylcellulose in 50 ml of ethanol are made into a paste, and this is dried and screened and subsequently mixed with 10 g of sodium sulphite.

Example 6

The procedure is analogous to Example 5, but sodium disulphite is used in place of sodium sulphite.

Examples 7–12

The procedure is analogous to Examples 5 or 6, but nitrocellulose, cetyl alcohol and paraffin, respectively, are employed in place of ethylcellulose.

Use Example A Self-Tanning Cream (O/W)

|   |   | % |
|---|---|---|
| A Emulsifier E 2155 | (2) | 8.0 |
| Liquid paraffin (Article No. 7162) | (1) | 12.0 |
| Pourable paraffin (Article No. 7158) | (1) | 2.0 |
| Miglyol 812 | (3) | 3.0 |
| Isopropyl myristate | (4) | 2.0 |
| B 1,2-propanediol (Article No. 7478) | (1) | 4.0 |
| Liquid Karion F (Article No. 2993) | (1) | 2.0 |
| Preservative | | q.s. |
| Demineralized water | | to 100.0 |
| C DHA powder prepared as described in Example 1 | (1) | 5.0 |
| Demineralized water | | 2.0 |

Preparation:

Heat phase A to 75° C. and phase B to 80° C. Slowly stir phase B into phase A. Cool while stirring, add phase C when the mixture has reached 40° C.

Note:

The samples contain 0.05% of propyl 4-hydroxybenzoate (Merck Article No. 7427) and 0.15% of methyl 4-hydroxybenzoate (Merck Article No. 6757)

as preservatives.

Suppliers:
1. E. Merck, Darmstadt
2. Th. Goldschmidt, Essen
3. Hüls Troisdorf AG, Witten
4. Henkel, Düsseldorf Use Example B Self-Tanning Milk (O/W)

|   |   |   | % |
|---|---|---|---|
| A | Arlatone 983 S | (2) | 1.50 |
|   | Arlatone 985 | (2) | 2.20 |
|   | Brij 76 | (2) | 1.50 |
|   | Liquid paraffin (Article No. 7162) | (1) | 5.00 |
|   | Miglyol 812 | (3) | 5.00 |
| B | Liquid Karion F (Article No. 2993) | (1) | 2.50 |
|   | 1,2-propanediol (Article No. 7478) | (1) | 2.50 |
|   | Preservative | (1) | q.s. |
|   | Demineralized water |   | to 100.00 |
| C | DHA powder prepared as described in Example 2 | (1) | 5.50 |
|   | Demineralized water |   | 14.50 |

Preparation:

Heat phase A to 75° C. and phase B to 80° C. Slowly stir phase B into phase A. Homogenize. Cool with stirring, add phase C when mixture has reached 40° C.

Note:

Viscosity 14,000 mPas (Brookfield RVT, Sp. C 10 rpm) at 23° C.

The samples contain 0.05% of propyl 4-hydroxybenzoate (Merck Article No. 7427) and 0.15% of methyl 4-hydroxybenzoate (Merck Article No. 6757)

as preservatives.

Suppliers:
1. E. Merck, Darmstadt
2. ICI, Essen
3. Hüls Troisdorf AG, Witten

Use Example C Self-Tanning Milk (W/O)

|   |   |   | % |
|---|---|---|---|
| A | Arlacel 481 | (2) | 3.15 |
|   | Arlacel 989 | (2) | 3.85 |
|   | Low-viscosity paraffin (Article No. 7174) | (1) | 16.00 |
|   | Isopropyl myristate | (3) | 3.50 |
|   | Miglyol 812 | (4) | 3.50 |
| B | 1,2-Propanediol (Article No. 7478) | (1) | 3.50 |
|   | Magnesium sulphate heptahydrate (Article No. 5882) | (1) | 0.70 |
|   | Preservative | (1) | q.s. |
|   | Demineralized water |   | to 100.00 |
| C | DHA powder prepared as described in Example 1 | (1) | 5.50 |

Preparation:

Heat phases A and B to 75° C. To avoid heat stress of the DHA powder by prolonged heating, phase C is dissolved in phase B and the solution is stirred into phase A. Homogenize. Cool rapidly with stirring to 25° C.

Note:

The samples contain 0.05% of propyl 4-hydroxybenzoate (Merck Article No. 7427) and 0.15% of methyl 4-hydroxybenzoate (Merck Article No. 6757)

as preservatives.

Suppliers:
(1) E. Merck, Darmstadt
(2) ICI, Essen
(3) Henkel, Düsseldorf
(4) Hüls Troisdorf AG, Witten Use Example D Self-Tanning Cream (O/W)

|   |   |   | % |
|---|---|---|---|
| A | Lanette N | (2) | 15.00 |
|   | Cetyl alcohol (Article No. 989) | (1) | 2.00 |
|   | Cetyl palmitate (Article No. 15419) | (1) | 5.00 |
|   | Corona lanolin | (3) | 0.50 |
|   | Cetiol | (2) | 5.00 |
|   | Petroleum jelly | (4) | 3.00 |
|   | Oxynex 2004 (Article No. 6940) | (1) | 0.05 |
| B | Liquid Karion F (Article No. 2993) | (1) | 3.00 |
|   | Preservative |   | q.s. |
|   | Demineralized water |   | to 100.00 |
| C | DHA powder prepared as described in Example 3 | (1) | 5.50 |
|   | Demineralized water |   | 14.50 |

Preparation:

Heat phase A to 75° C. and phase B to 80° C. Slowly stir phase B into phase A. Homogenize. Cool with stirring, add phase C when mixture has reached 40° C. and, if appropriate, perfume.

Note:

The samples contain 0.05% of propyl 4-hydroxybenzoate (Merck Article No. 7427) and 0.15% of methyl 4-hydroxybenzoate (Merck Article No. 6757)

as preservatives.

Suppliers:
(1) E. Merck, Darmstadt
(2) Henkel, Düsseldorf
(3) Croda, Nettertal
(4) E. Wagner, Bremen Use Example E Self-Tanning Cream (O/W)

|   |   |   | % |
|---|---|---|---|
| A | Arlacel 165 | (2) | 6.60 |
|   | Atlas G-1790 | (2) | 3.60 |
|   | Lanette O | (3) | 3.00 |
|   | Liquid paraffin (Article No. 7162) | (1) | 1.50 |
|   | Isopropyl myristate | (3) | 4.00 |
|   | Abil AV 200 | (4) | 1.00 |
|   | Oxynex 2004 (Article No. 6940) | (1) | 0.05 |
| B | Liquid Karion F (Article No. 2993) | (1) | 6.00 |
|   | Preservative |   | q.s. |
|   | Demineralized water |   | to 100.00 |
| C | DHA powder prepared as described in Example 4 | (1) | 5.50 |
|   | Demineralized water |   | 14.50 |

Preparation:

Heat phase A to 75° C. and phase B to 80° C. Slowly stir phase B into phase A. Homogenize. Cool while stirring, add phase C when the mixture has reached 40° C. and, if appropriate, perfume.

Note:

The samples contain 0.05% of propyl 4-hydroxybenzoate (Merck Article No. 7427) and 0.15% of methyl 4-hydroxybenzoate (Merck Article No. 6757)

as preservatives.

Suppliers:

(1) E. Merck, Darmstadt
(2) ICI, Essen
(3) Henkel, Düsseldorf
(4) Th. Goldschmidt, Essen Use Example F Self-Tanning Gel (Aqueous)

|   |   | % |
|---|---|---|
| A DHA powder prepared as described in Example 1 | (1) | 5.50 |
| Liquid Karion F (Article No. 2993) | (1) | 2.50 |
| 1,2-Propanediol (Article No. 7478) | (1) | 2.50 |
| Preservative |  | q.s. |
| Demineralized water |  | to 100.00 |
| B Natrosol 250 HHR | (2) | 1.50 |
| Demineralized water |  | 60.00 |

Preparation:

To prepare phase B, Natrosol is slowly added to the eddy of the vigorously stirred water. The addition is effected slowly and uniformly so that the particles can be distributed in water without lumps being formed. To prepare phase A, the DHA powder is stirred into the water, and the remaining raw materials are added, with stirring. This suspension is stirred into phase B, and the mixture is homogenized.

Note:

Slightly opaque gel

The samples contain 0.20% of methyl 4-hydroxybenzoate (Merck Article No. 6757) as preservative.

Storage at room temperature is recommended to avoid a reduction in viscosity from approximately 40° C.

Suppliers:

(1) E. Merck, Darmstadt
(2) Aqualon, Düsseldorf

In the formulations described in Use Examples A to F, no formaldehyde was detected after prolonged storage even at elevated temperature.

Comparison Example 1

A self-tanning cream (O/W) which corresponds to Use Example A is prepared, but in which the DHA powder according to the invention is replaced by:

a) pure DHA 5.00 g, or b) DHA coated in accordance with WO91/12222 5.00 g

After storage for 3 months at 40° C., the following concentrations of formaldehyde and formic acid are found:

|  | HCHO (ppm) | HCOOH (ppm) |
|---|---|---|
| Use Example A | n.d. | n.d. |
| a) | 70 | 3569 |
| b) | 70 | 5825 |

Comparison Example 2

A self-tanning milk (W/O) which corresponds to Use Example C is prepared, but in which the DHA powder according to the invention is replaced by:

a) pure DHA 5.00 g, or b) DHA coated in accordance with W091/12222 5.00 g

After storage for 3 months at 40° C., the following concentrations of formaldehyde and formic acid are found:

|  | HCHO (ppm) | HCOOH (ppm) |
|---|---|---|
| Use Example C | n.d. | n.d. |
| a) | 33 | 3438 |
| b) | 23 | 2365 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A powder mixture comprising (a) a compound having skin tanning properties which is dihydroxyacetone and (b) a source of sulfite ions which is sodium hydrogen sulphite, sodium disulphite or sodium dithionite.

2. A mixture according to claim 1, further comprising a stabilizer.

3. A mixture according to claim 2, comprising 45 to 99% by weight dihydroxyacetone, 0.1 to 50% by weight of the source of sulfite ions and 0.1 to 5% by weight of the stabilizer.

4. A mixture according to claim 1, further comprising a stabilizer, which is a stearate.

5. A mixture according to claim 1, further comprising a stabilizer, which is a cellulose derivative.

6. A mixture according to claim 2, comprising 80–90% by weight, of the compound having skin-tanning properties 1–20% by weight of the source of sulphite ions, and 0.1 to 5% by weight of the stabilizer.

7. A mixture according to claim 2, producible by a process comprising triturating, grinding together or partially coating the compound having skin-tanning properties, the source of sulfite ions, or both, with the stabilizer.

8. A mixture according to claim 7, wherein the source of sulphite ions is coated.

9. A mixture according to claim 2, producible by a process comprising triturating the compound having skin-tanning properties, the source of sulfite ions, or both, with a conventional lubricant.

10. A mixture according to claim 2, producible by a process comprising partially coating the compound having skin-tanning properties, the source of sulfite ions, or both, with a conventional film-forming agent.

* * * * *